US012507743B2

(12) United States Patent
Schwartz

(10) Patent No.: US 12,507,743 B2
(45) **Date of Patent: *Dec. 30, 2025**

(54) SYSTEM AND METHOD FOR DYNAMIC DEPLOYMENT OF SMART FACIAL PROTECTOR BASED ON NEED

(71) Applicant: Sean H. Schwartz, Ashburn, VA (US)

(72) Inventor: Sean H. Schwartz, Ashburn, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/915,784

(22) Filed: Oct. 15, 2024

(65) Prior Publication Data

US 2025/0031775 A1 Jan. 30, 2025

Related U.S. Application Data

(63) Continuation of application No. 17/992,505, filed on Nov. 22, 2022, now Pat. No. 12,133,564.

(60) Provisional application No. 63/282,864, filed on Nov. 24, 2021.

(51) Int. Cl.

| | |
|---|---|
| ***A41D 13/11*** | (2006.01) |
| ***A41D 1/00*** | (2018.01) |
| ***A61L 2/18*** | (2006.01) |

(52) U.S. Cl.
CPC .......... *A41D 1/002* (2013.01); *A41D 13/1161* (2013.01); *A41D 13/1184* (2013.01); *A61L 2/18* (2013.01); *A61L 2202/15* (2013.01)

(58) Field of Classification Search
CPC .... A41D 1/002; A41D 13/11; A41D 13/1184; A42B 3/22; A42B 3/224; A61L 2/18; A61L 2202/15; A61B 5/7275; G16H 50/80
See application file for complete search history.

(56) References Cited

U.S. PATENT DOCUMENTS 4,875,477 A * 10/1989 Waschke ............ A61B 5/02438 128/206.26
4,986,282 A * 1/1991 Stackhouse ............... A61F 9/02 128/857
5,086,515 A * 2/1992 Giuliano ................. A61F 9/027 2/8.1
11,045,271 B1 * 6/2021 Tran ........................ G16H 20/40
2003/0028953 A1 * 2/2003 Acquaviva ............. A42B 3/224 2/429

(Continued)

FOREIGN PATENT DOCUMENTS

CN 113677229 B * 2/2024 ......... A41D 13/1184

*Primary Examiner* — Jillian K Pierorazio
(74) *Attorney, Agent, or Firm* — Venable LLP

(57) ABSTRACT

The present teaching relates to a protector capable of dynamically deploying protection to a user. Data is received from multiple sensors embedded in the protector, worn by a user on head and providing protection to the user when needed. Distances between the user and others appearing nearby detected based on the data are dynamically tracked. If the protector is in a protection state, the protection is retracted when the tracked distances satisfy a first condition. The state of the protector is reset to a no-protection state. If the protector is in a no-protection state, the protector applies the protection to the user, when a second condition is satisfied based on the tracked distances, by releasing one or more protection shields from the protector to create a barrier between the user and others and the state of the protector is reset to a protection state.

16 Claims, 26 Drawing Sheets

(56) References Cited

U.S. PATENT DOCUMENTS

| | | | | |
|---|---|---|---|---|
| 2013/0191976 | A1* | 8/2013 | Pizzi | A42B 3/223<br>2/424 |
| 2013/0219599 | A1* | 8/2013 | Garcia | A42B 3/22<br>2/424 |
| 2015/0320135 | A1* | 11/2015 | Lowe | A42B 3/22<br>2/411 |
| 2016/0184469 | A1* | 6/2016 | Welch | G06V 20/52<br>348/143 |
| 2020/0265701 | A1* | 8/2020 | Schenker | G01C 21/36 |
| 2021/0283293 | A1* | 9/2021 | Sonovani | A61L 2/18 |
| 2022/0218051 | A1* | 7/2022 | Saleh | G01K 3/005 |
| 2022/0369735 | A1* | 11/2022 | Ali | A41D 13/1184 |
| 2023/0284714 | A1* | 9/2023 | Chahine | A41D 13/11 |
| 2024/0016455 | A1* | 1/2024 | Pinczuk | A61B 5/7275 |

* cited by examiner

SYSTEM AND METHOD FOR DYNAMIC DEPLOYMENT OF SMART FACIAL PROTECTOR BASED ON NEED

CROSS REFERENCE TO RELATED APPLICATIONS

The present application is a continuation of U.S. patent application Ser. No. 17/992,505, filed on Nov. 22, 2022, which claims the benefit and priority of U.S. Provisional Patent Application No. 63/282,864, filed on Nov. 24, 2021, the contents of which are hereby incorporated by reference in their entireties.

BACKGROUND

1. Technical Field

The present teaching generally relates to protector. More specifically, the present teaching relates to face protector.

2. Technical Background

A human body is largely sealed from the outside environment except a few limited opened organs such as mouth, nose, ears, and eyes. Bacteria and viruses are often invading into a human body through such open organs, causing different infectious diseases such as cold, flu, or others. From the Spanish flu in early 20th century to SARS in 2002, Swine flu in 2010, MERS in 2012, and the ongoing COVID-19 starting in 2020, they are all transmitted through these open organs. In addition to these world-wide health events, the human population each year still battles with cold and general flu, which also caused different degrees of human suffering and ultimately many deaths. Although the modern medicine tries to come up with vaccines for different viruses, the new variants or even brand-new viruses still emerge at a seemingly increased speed.

To protect people from such harmful bacteria/viruses, it has been known for a long time to cover these open organs. A few commonly used means to cover different parts of the head. For example, in FIG. 1A, a face mask 110 can be used to cover a person's nose and mouth. Modern masks may be designed to have specific fabrics that can block bacteria or viruses of certain sizes from penetrating. As another example, to cover eyes, glasses such as 120 in FIG. 1B may be used to prevent harmful matters from entering eyes. During the 2020 pandemic of COVID-19, face shields emerged which can be worn like a hat as shown in FIG. 1C where a physical shield 140 from a rim 130 and going down to the neck area. While all these means may be used to protect different parts, they are designed to be cover either only some part of the face or once worn they are there all the time. Although any of such covers may be taken down when needed, it is often the case that once it is taken down, it either needs to be throw away or have to be sanitized fully using special means because the side of the device facing the outside world may have been contaminated. This may have the opposite effect when a person does not fully sanitize a protective device that has some parts already contaminated.

There may have other potential issues. For example, wearing a mask makes it difficult for the person to breath in adequate amount of fresh air, reducing the amount of oxygen the person can have. This is especially so when the person wears a mask all day long such as medical personnel working in a hospital. The problem can be more serious when the person is physically active. There have been reported cases where people wearing masks when they are doing exercises at gyms and passed out due to lack of oxygen. Although a face shield may not block as much as fresh air as a mask, the same issue still exists because a face shield does create a barrier to prevent the person from freely breathing in fresh air.

Thus, there is a need for a solution that address the shortcomings and enhance the performance of these traditional protectors.

SUMMARY

The teachings disclosed herein relate to methods, systems, and programming for information management. More particularly, the present teaching relates to methods, systems, and programming related to hash table and storage management using the same.

In one example, a method, implemented on a machine having at least one processor, storage, and a communication platform capable of connecting to a network for dynamically deploying protection to a user. Data are received from a plurality of sensors embedded in the protector, worn by a user on head and for providing protection to the user based on need. The data capture information surrounding the protector and are used to detect a closest distance associated with a person among one or more people appearing nearby the user. If the closest distance satisfies a first condition, the protector applies protection to the user via at least one protection sheet stored in the protector to create a barrier between the user and the one or more people In a different example, a protector is disclosed for dynamically deploying protection to a user. The protector comprises a head band constructed for being worn by a user around the head. The protector is embedded with at least one protection sheet. Each of the at least one protection sheet is constructed with flex material so that it can be rolled up into a designated storage embedded in the head band and rolled down to create a barrier between the head of the user wearing the protector and surrounding environment, provided to protect a designated part of the user, and can be separately sanitized when it is either rolled up or rolled down. The protector is also embedded with a plurality of sensors embedded around the perimeter of the head band and configured for monitoring surrounding of the user to facilitate dynamic deployment of the at least one protection sheet to protect the user when needed.

Other concepts relate to software for implementing the present teaching. A software product, in accordance with this concept, includes at least one machine-readable non-transitory medium and information carried by the medium. The information carried by the medium may be executable program code data, parameters in association with the executable program code, and/or information related to a user, a request, content, or other additional information.

Another example is a machine-readable, non-transitory and tangible medium having information recorded thereon for dynamically deploying protection to a user. The information, when read by the machine, causes the machine to perform the following steps. Data are received from a plurality of sensors embedded in the protector, worn by a user on head and for providing protection to the user based on need. The data capture information surrounding the protector and are used to detect a closest distance associated with a person among one or more people appearing nearby the user. If the closest distance satisfies a first condition, the protector applies protection to the user via at least one protection sheet stored in the protector to create a barrier between the user and the one or more people.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
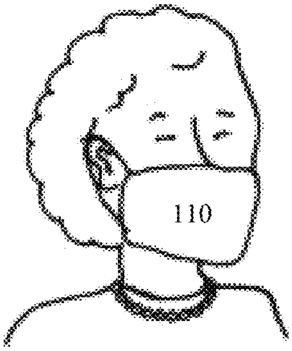
FIGS. 1A-1C provide examples of traditional covering mechanisms to protect open organs of a person.
Figure 1B:
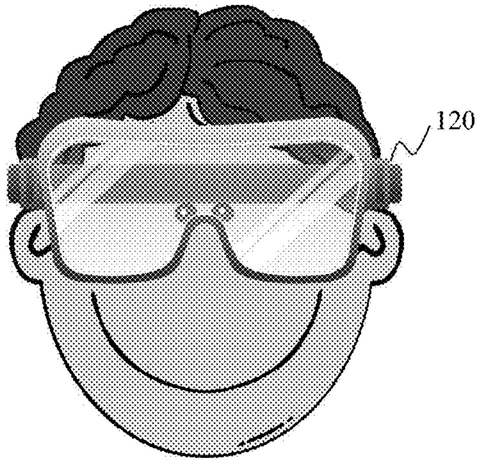
Figure 1C:
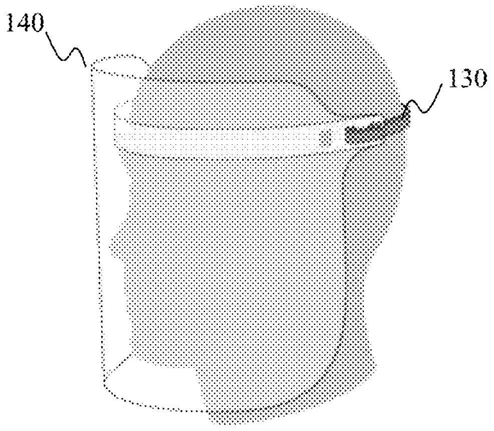

In the following detailed description, numerous specific details are set forth by way of examples in order to facilitate a thorough understanding of the relevant teachings. However, it should be apparent to those skilled in the art that the present teachings may be practiced without such details. In other instances, well known methods, procedures, components, and/or system have been described at a relatively high-level, without detail, in order to avoid unnecessarily obscuring aspects of the present teachings.

The present teaching is directed to a smart multi-function protector that can be adaptively activated/deactivated to protect different parts of a person based on a situation detected automatically from the surroundings of the person. The smart multi-function protector overcome the problems of having to wear a mask/shield all the time, causing lower level of oxygen, and the risks of re-use if required caution associated with taking down the mask/shield is not performed correctly. A person may wear the smart multi-function protector, but the protection may be applied only when certain conditions are met. In some embodiments, the condition of deploying the protection may be based on whether someone is detected in a certain distance range. When the condition is not met, the smart protector as disclosed herein may be configured to withdraw the protection applied previously or without applying the protection if no protection is applied previously. In this way, the person wearing the smart protector is not deprived of adequate amount of oxygen because of the constant application of the protection, especially when the person is in an environment with much reduced risks.

The smart protector according to the present teaching includes multiple flexible protection sheets, each of which may be provided to protect a certain organ (e.g., nose and mouth). Each of the protection sheet may be stored or rolled up in a storage when no protection is needed and released (rolled down) from the storage when protection is initiated. The dimension of each of the protection sheet may vary according to the intended organ to be protected and the location of the organ. For some examples, the protection sheet for protecting the nose and mouth may be longer when released, while the protection sheet for protecting eyes and ears may be shorter but wider due to the locations of the ears.

To automate adaptive initiation of the protection, in some embodiments, a certain distance related criterion may be defined, e.g., a safety radius within which is another person is detected, the protection is initiated. To enable that, a band of the smart protector which can rest on a person's head may be embedded with sensors that are deployed around the band to detect the surrounding of the person. In some embodiments, such sensors may be visual and the acquired visual data may be used to detect whether a surrounding object corresponds to another person. Such visual data may also be used to estimate the distance to another person based on, e.g., stereo techniques. In some embodiments, depth sensor may also be deployed which may provide depth data of each surrounding object. In some embodiments, visual and depth sensors may both be deployed and used to visually detect other surrounding people and then using the sensor data from the depth sensor to obtain the distance to each of such surrounding people. The safety distance may be dynamically configured by a user so that the degree of protection may be personalized.

To ensure that the protection sheets are free from bacteria/viruses, whenever a protection sheet is stored or released, it may be automatically sanitized to ensure that what is used to protect the person does not itself create an unsafe local atmosphere inside of the protector for the person. To do so, the smart protector is equipped with sanitization means which may be an ultraviolet radiation mechanism to shine on the protection sheet or spray mechanisms that can be activated to spray sanitizing liquid such as alcohol on different sides of the protection sheets. In some embodiments, when a protection sheet is rolled down or released to apply the protection, the sanitization may be applied to be directed to the internal side of the protection sheet. When the protection sheet is rolled up for storage when the protection is no longer needed, the sanitization may be applied to both sides of each protection sheet to ensure that whatever is stored is free of bacteria/viruses. The sanitization means may be embedded in the smart protector and distributed around the band of the protector in a manner that they provide a full coverage to the protection sheet to be sanitized.

Figure 2A:
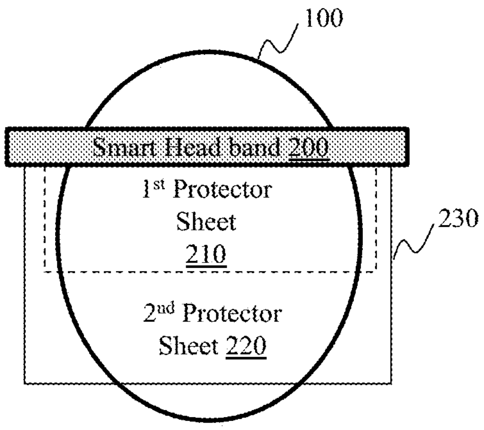
FIG. 2A depicts a frontal view of a smart multi-function protector, in accordance with an embodiment of the present teaching.

FIG. 2A depicts a frontal view of a smart multi-function protector 230, in accordance with an embodiment of the present teaching. As can be seen, the smart multi-function protector 230 is placed on the head of a person 100. The smart multi-function protector 230 includes a smart head band 200, a first protection sheet 210 and a second protection sheet 220. In some embodiment, the $1^{st}$ protection sheet 210 may be provided to protect the upper part of a face and specifically can create a shield between eyes and/or ears and outside of the face. The $2^{nd}$ protection sheet 220 may be provided to protect the person wearing the protector, including the nose, the mouth, the eyes, and/or ears of the person. In some embodiments, the $1^{st}$ and $2^{nd}$ protection sheets may be released separately. For instance, the $2^{nd}$ protection sheet may be deployed to protect all organs on the head. In some situations, the $1^{st}$ protection sheet may be applied to protect only eyes and ears without applying the $2^{nd}$ protect layer to segregate the nose and mouth from outside. In some embodiments, both the $1^{st}$ and $2^{nd}$ protection sheets may be applied so that not only all open organs on the head are protected, the eyes and possibly ears may be protected by two layers of protection sheets.

Figure 2B:
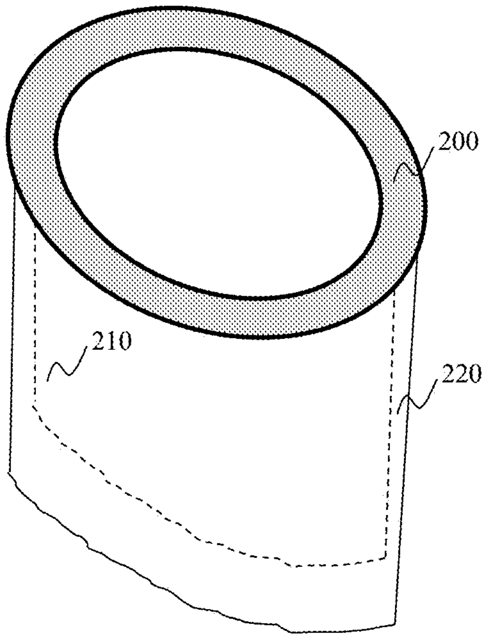
FIG. 2B depicts a top view of a smart multi-function protector, in accordance with an embodiment of the present teaching.

FIG. 2B depicts a top view of the smart multi-function protector 230, in accordance with an embodiment of the present teaching. As shown, the smart head band 200 of the smart multi-function protector 230 is a structure shaped like a circle so that it can be worn or rest on a person's head. The $1^{st}$ protection sheet 210 may be released from a track (discussed below) located on the smart head band 200 along the perimeter of the head band. The $1^{st}$ protection sheet may not be all the way around the head band as the open organs to be protected are not present in the back of the person's head. For example, it may be wrapped around to make sure that ears can be protected. As another example, the $1^{st}$ protection sheet may warp around just enough to protect only eyes without covering the ears. However, it may also be all the around to provide extra protection. The design is application dependent.

Similarly, the $2^{nd}$ protection sheet is stored and can be released in/from a different track of the smart head band (discussed below) residing at an outer layer of the smart head band so that the $2^{nd}$ protection sheet is between the $1^{st}$ protection sheet and outside world when deployed. The $2^{nd}$ protection sheet may or may not be all the way around the smart head band for the same reasons as discussed herein with respect to the $1^{st}$ protection sheet. It is possible to use the $2^{nd}$ protection sheet to protect the ears by wrapping the $2^{nd}$ sheet to cover the ears. If that is the design, then the $1^{st}$ protection sheet may be provided in a manner with protection only to the eyes. The lengths (from the head band to the end of a released protection sheet) of the $1^{st}$ and $2^{nd}$ protection sheets may also vary, depending on what each is intended to protect. For instance, if ears are to be protected by the $2^{nd}$ protection sheet, the length of the $1^{st}$ protection sheet may be made shorter and can be much closer to the eyes when released and hence with better protection. The length of the $2^{nd}$ protection sheet may also be designed based on needs, e.g., may cover a person's face all the way to the chin or even neck of the person.

Figure 2C:
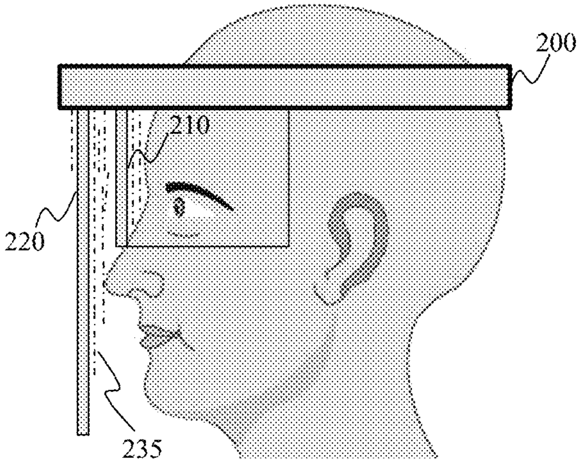
FIG. 2C depicts a side view of a smart multi-function protector, in accordance with an embodiment of the present teaching.
Figure 2D:
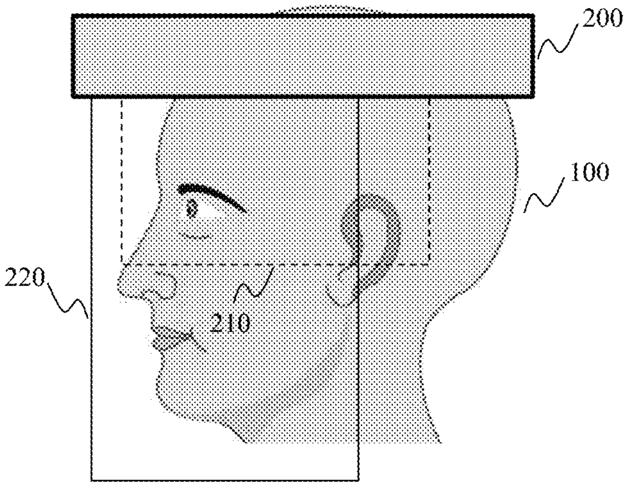
FIG. 2D depicts an alternative exemplary construct and components of a smart multi-function protector, in accordance with an embodiment of the present teaching.

FIG. 2C depicts a side view of the smart multi-function protector 230, in accordance with an embodiment of the present teaching. In this side view, the $1^{st}$ and $2^{nd}$ protection sheets are shown to be released to cover the open organs that each in intended to protect. In this view, the smart head band includes different tracks from which the $1^{st}$ and $2^{nd}$ protection sheets can be rolled up to be stored in the head band 200 or can be released from these tracks to segregate these open organs from the outside environment. As illustrated, $1^{st}$ protection sheet 210 is located between the eyes of the person and the $2^{nd}$ protection sheet 220. As discussed herein, the $1^{st}$ protection sheet has a length, which is determined based on the open organs to be protected. In this illustration, the $1^{st}$ protection sheet is to protect the eyes (without ears) so that it ends at the nose. If the $1^{st}$ protection sheet is also to protect ears, the $1^{st}$ protection sheet needs to be longer to cover the ears. In addition, the $1^{st}$ protection sheet 210 may need be pushed out further from the face to pass the nose region to continue to expand lower. FIG. 2D provides a different example in which the $1^{st}$ protection sheet extends further around the perimeter of the head band 200 to cover the ears of the person and the $2^{nd}$ protection sheet 220 may or may not be provided also to cover the ears of the person.

Due to the construct of a human head, the $2^{nd}$ protection sheet 220 is at the outer layer than that of the $1^{st}$ sheet 210 and can be separately released form the head band 200. As the $2^{nd}$ protection sheet is for provide the nose and mouth, it is longer to pass the mouth region. Both the $1^{st}$ and $2^{nd}$ protection sheets may be stored in and released from the headband 200 and they need to be sanitized to make sure that it creates a safe environment for the person to be protected. As discussed herein, the protection sheets can be sanitized either via ultraviolet radiation inside of the storage embedded in the head band or by spraying sanitizing liquid such as alcohol to the protection sheets. The spray of sanitizing liquid 235 is shown in FIG. 2C, where the spray may be applied to both sides of the protection sheets.

Figure 2E:
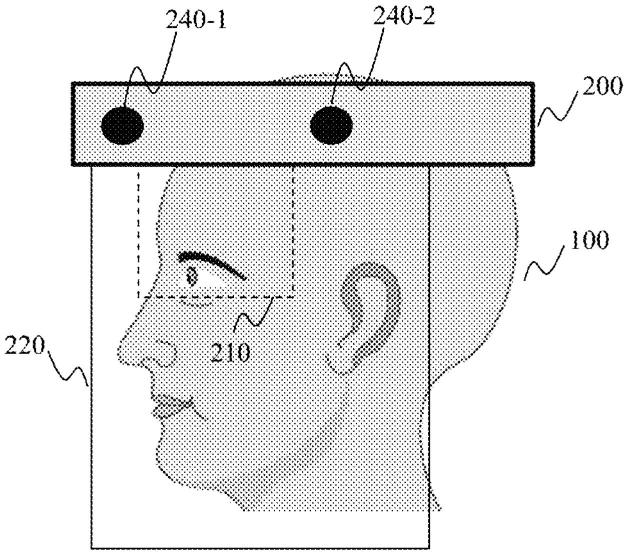
FIG. 2E depicts an exemplary construct and components of a smart multi-function protector, in accordance with an embodiment of the present teaching.

FIG. 2E depicts an exemplary construct with some components of the smart multi-function protector 230 embedded in the head band, in accordance with an embodiment of the present teaching. In this illustration, the 1$^{st}$ protection sheet 210 is for protecting eyes and the 2$^{nd}$ protection sheet 220 is to protect the nose, mouth, and the ears. The protection is activated dynamically whenever there is a need so that the protection sheets may not be there all the time so that the person can still have adequate amount of oxygen. To determine when the protection sheets need to be released to apply protection, the head band 200 is embedded with multiple sensors 240-1, . . . , 240-2 for monitoring the surrounding of the person wearing the smart multi-function protector 230. Such sensors may be visual sensor or depth sensor or any other sensors operating in other modalities. The sensors employed are for detecting presence of other people in a specified range and optionally the specific distances of such nearby individuals.

Figure 3A:
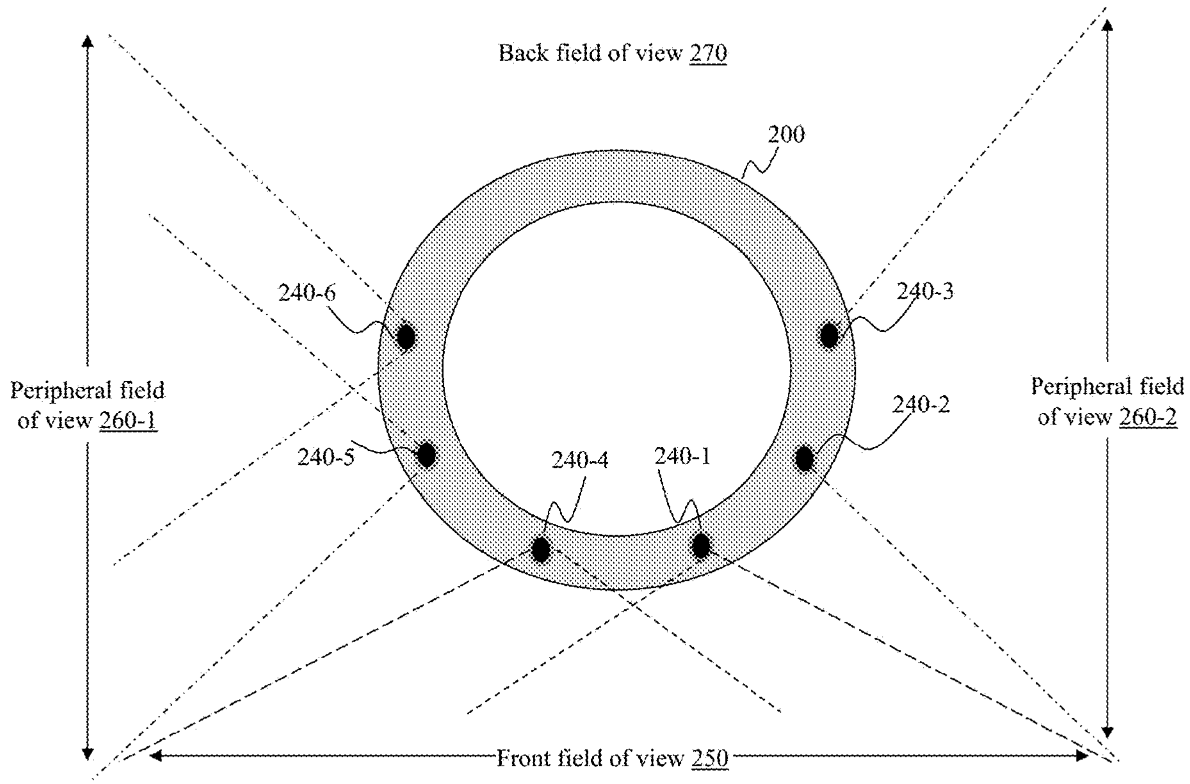
FIG. 3A depicts an exemplary distribution of sensors in a smart multi-function protector, in accordance with an embodiment of the present teaching.

FIG. 3A depicts an exemplary distribution of sensors in the smart multi-function protector 230 for monitoring surrounding of a person, in accordance with an embodiment of the present teaching. In this illustration, there are different sensors, e.g., 240-1, 240-2, 240-3, 240-4, 240-5, and 240-6, arranged in the head band 200 to provide a monitoring coverage around the person in the front and the two sides. In some embodiments, more sensors may also be installed in the back as well in order to provide a coverage of a full 360 degrees around the person. The sensors in the head band are deployed in such a density and positioned in a way to ensure coverage. For instance, if visual sensors are used, the field of view of different sensors will cover the area to be monitored. As shown in FIG. 3A, the two cameras 240-1 and 240-4 in the front provide a frontal field of view 250, cameras 240-5 and 240-6 provide the first peripheral field of view 260-1, and cameras 240-2 and 240-3 provide a second peripheral field of view 260-2. These cameras together provide a full coverage of monitoring for the front and two side views of the person.

Figure 3B:
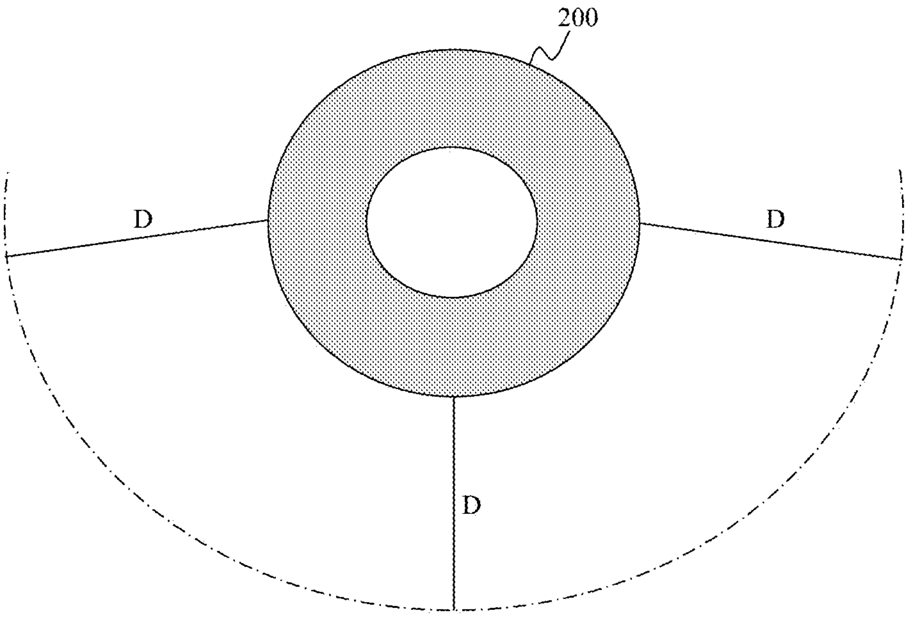
FIG. 3B shows an exemplary safety zone in which a detected approaching human may trigger automated deployment of protection, in accordance with an exemplary embodiment of the present teaching.

Monitoring the surroundings is for determine when the protection sheets need to be released to apply protection. The determination is made with respect to, e.g., when there are others within a distance from the person to be protected that is within a set distance threshold to initiate protection. Such a distance threshold may be configured for each smart multi-function protector by the individual wearing it. FIG. 3B illustrates an example way to define a coverage of an area of a person to be protected by the smart multi-function protector 230, in accordance with an exemplary embodiment of the present teaching. In this illustration, a radius D from the head band 200 of the smart multi-function protector 230 is define as the distance threshold, i.e., if anyone is detected within radius D around a person wearing the protector 230, the protection to the person is initiated, i.e., the protection sheet(s) may be released. Given that, the detection of the surrounding may be initiated by the person wearing the protector and continue to operate in order to be aware of the surroundings.

Figure 3C:
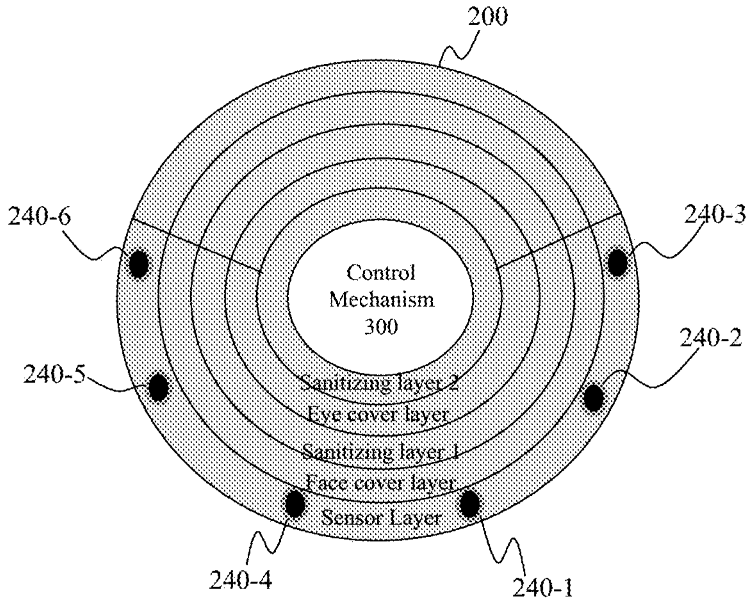
FIG. 3C depicts exemplary internal layers in a frontal part of a smart multi-function protector, in accordance with an embodiment of the present teaching.

FIG. 3C depicts exemplary internal layers in a frontal part of a smart multi-function protector, in accordance with an embodiment of the present teaching. As discussed herein, the smart multi-function protector 230 may be with sensors at a sensor layer at the outer layer of the head band 200. To enable the operation of the protector 230, additional components may also be embedded and deployed in the protector 230. This is illustrated in FIG. 3C. For instance, the head band of the protector 230 may be constructed to have storages for the 1$^{st}$ and 2$^{nd}$ protection sheets with the capability of rolling the sheets up into the storage and release the sheet out of the storage. In such storages, it may be provided with protection sheets that are made with transparent materials that are flexible enough to be rolled (either in or out). In addition, the materials used for the sheets are such that, once rolled in, the sheets can stay in a rolled fashion but when they are rolled out, the sheets remain flat so that the sheets hold up in a vertical direction.

To sanitize the protection sheets, the head band may also include mechanisms for that purpose. As discussed herein, the sanitization may be performed via ultraviolet radiation on the sheets in which case, the head band may incorporate miniaturized ultraviolet radiation mechanisms for that purpose. In some embodiments, sanitizing may be performed by spraying sanitizing liquid such as alcohol. In this case, the head band may include sanitizing layers corresponding to the protection sheet layers. In those sanitizing layers, depending on the sanitizing method, either ultraviolet radiation mechanism or some liquid spraying means may be deployed at different layers, e.g., interleaved with the protection sheet layers. In the situation that ultraviolet sanitization approach is used, the materials used to construct the head band may be selected in such a way that will securely block the ultraviolet radiation rays from reaching the person. In the situation that sanitizing mean is via spraying sanitizing liquid, the head band may be equipped with spray heads at different locations and layers that can be controlled and configured.

Furthermore, to control the operation of the protector 230, the head band may also be equipped with a control mechanism 300, which may be implemented with a microprocessor and embedded at, e.g., the top of the protector, to, e.g., issue command to control the initiation or end of the protection by releasing or rolling up of either of the protection sheets, sanitizing when needed in different situations (e.g., sanitizing during release and roll up may be operated in different ways). Such control decisions may be made based on what is observed from the surroundings so that the control mechanism 300 may also include some functional processes that process the sensor data and make determination on what is present in the surroundings. In some embodiments, to minimize the processing performed on the protector 230 (e.g., to minimize the weight of the protector or to reduce the need for local battery power), the control mechanism 300 may include be configured differently. In some embodiments, the control mechanism 300 may be configured to transmit sensor data to a server located in the nearby rooms so that the computation of the sensor data is carried out by the server, which can then send a control signal to the control mechanism 300 to, release or roll up the protection sheets to initiate or end the protection. In some embodiments, the control mechanism 300 may include only function to extract features from the sensor data locally and send such extracted features to the server to make a control decision based on more complicated algorithms. In this way, the data bandwidth needed is reduced. In some embodiments, all the computation may be performed on the control mechanism 300. In this illustrated embodiment in FIG. 3C, the control mechanism 300 may be located on the top of the protector, which may not be considered as part of the head band, which is around the perimeter of the head of the person.

Figure 3D:
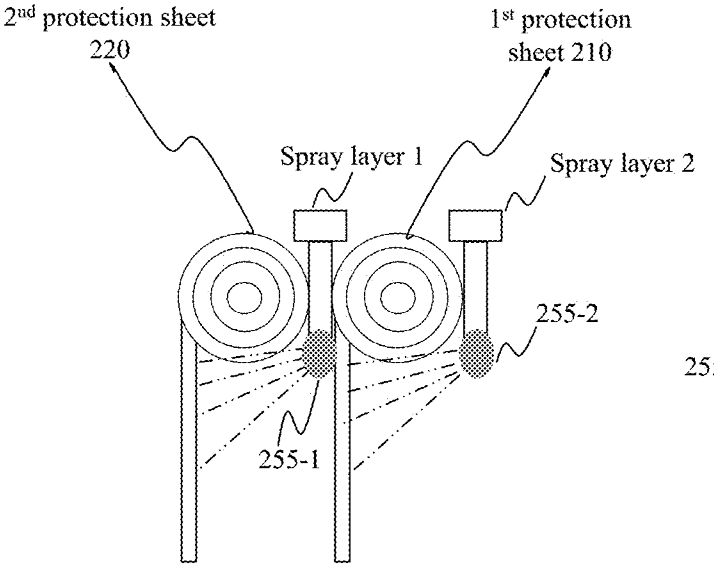
FIGS. 3D-3E illustrate the exemplary mechanism to disinfect different layers of covers with controllable disinfectant spray directions to sanitize different parts of a smart multi-function protector, in accordance with an embodiment of the present teaching.
Figure 3E:
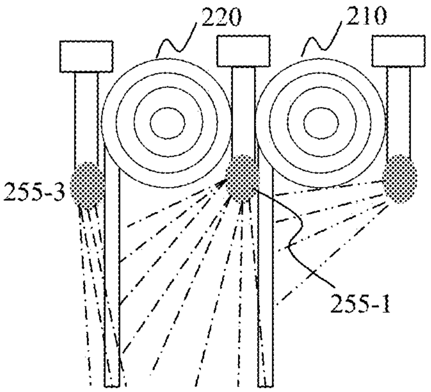

As discussed herein, the smart multi-function protector 230 may adopt different means to sanitize needed sides of the protection sheets. In some embodiments, this may be done via ultraviolet radiation. In some embodiments, it may be carried out via spraying sanitizing liquid. In some embodiments, the ultraviolet radiation and disinfectant liquid spraying may be used in combination, e.g., using ultraviolet radiation to the interior sides of the protection sheets because it is directed to the exterior region of the person but using liquid spraying to the exterior side of the protection sheets because it is directed to the direction of the person's face. FIGS. 3D-3E illustrate exemplary configurations to sanitize different layers of the protection sheets via disinfectant spraying, in accordance with an embodiment of the present teaching. Each protection sheet can be stored in storage by rolling up as shown in FIG. 3D. As each protection sheet has two sides, when it is rolled down, one side facing the person's face and the other side facing outward. FIG. 3D illustrates an exemplary construct as shown where there are two storages for storing the $1^{st}$ and $2^{nd}$ protection sheets when rolled up. Next to each storage, there may be deployed with spray layer 1 and spray layer 2, interleaved with the storage space. On each of the spray layer, there are multiple spray heads, e.g., 255-1 and 255-2 as shown, each of which may have spray holes thereon with, e.g., valves inside that can be controllable to close or open at different angles and/or degrees in order to control how the disinfectant is sprayed as mist in a certain direction with a certain desired strength. The spray heads may be configured to roll with different angles as part of controlling the direction of the spray mist.

FIG. 3D illustrates how the sprays heads at each spray layer may spray the mist of disinfectant in a direction towards the interior side of a protection sheet while the protection sheet is being rolled down from the storage. In this way, when a person needs protection, the smart multi-function protector 230 controls to roll down the $1^{st}$ protection sheet 210 closer to the face and/or the $2^{nd}$ protection sheet 220 and at the same time to control the spray heads at spray layer 1 and/or spray layer 2 to mist the interior sides of the protection sheets to ensure sanitized atmosphere closer to the person's face. FIG. 3E illustrated how the spray heads at different spray layers can be controlled to sanitize the protection sheets when they are rolled up to be stored in the storages. As discussed herein, before the protection sheets are rolled into the protector 230, both sides of the protection sheets may need to be sanitized. In this case, there may be an additional spray layer 3 with spray heads such as 255-3 designed for spray disinfectant to the exterior side of the $2^{nd}$ protection sheet. At the same time, the spray heads at the spray layer 1 may be controlled to spray at an angle in such a way that it will cover both the interior side of the $2^{nd}$ protection sheet and the exterior side of the $1^{st}$ protection sheet, as shown in FIG. 3E. In addition, the spray heads on the spray layer 2 may be controlled in a similar mode as what is shown in FIG. 3D to spray the disinfectant in the direction to reach and cover the interior side of the $1^{st}$ protection sheet 210.

Figure 3F:
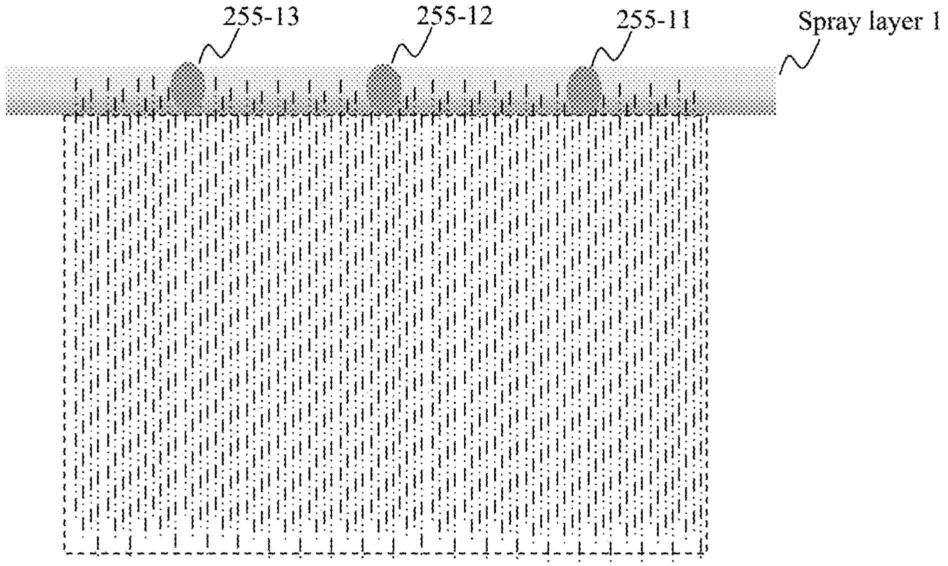
FIG. 3F illustrates an exemplary disinfectant spray coverage on a protection sheet from a vertical direction, in accordance with an embodiment of the present teaching.

FIG. 3F describes a different implementation of a spray layer, in accordance with an embodiment of the present teaching. In this implementation, a spray layer, e.g., spray layer 1, can be a construct with distributed sweating holes which can be controlled to oozing out disinfectant like a sweating hose to drip the liquid over one side of a protection sheet below. For example, spray layers 1 and 3 as shown in FIG. 3E may be implemented with distributed sweating holes so that the disinfectant can drip to the exterior side of the $1^{st}$ and $2^{nd}$ protection sheets. In this implementation, in addition to the distributed sweating holes, a spray layer may also have interleaved spray heads, e.g., 255-11, 255-12, . . . , 255-13 as shown in FIG. 3F, that are deployed to spray the disinfectant to the interior side of an adjacent protection sheet. For instance, spray layer 1 may be constructed to include both sweating holes and interleaved spray heads so that the exterior side of the $1^{st}$ protection sheet may be sanitized by activating the sweating holes and the interior side of the $2^{nd}$ protection sheet may be sanitized by activating the spray heads 255-11, 255-12, . . . , 255-13 to spray across the space to reach the interior side of the $2^{nd}$ protection sheet.

Figure 3G:
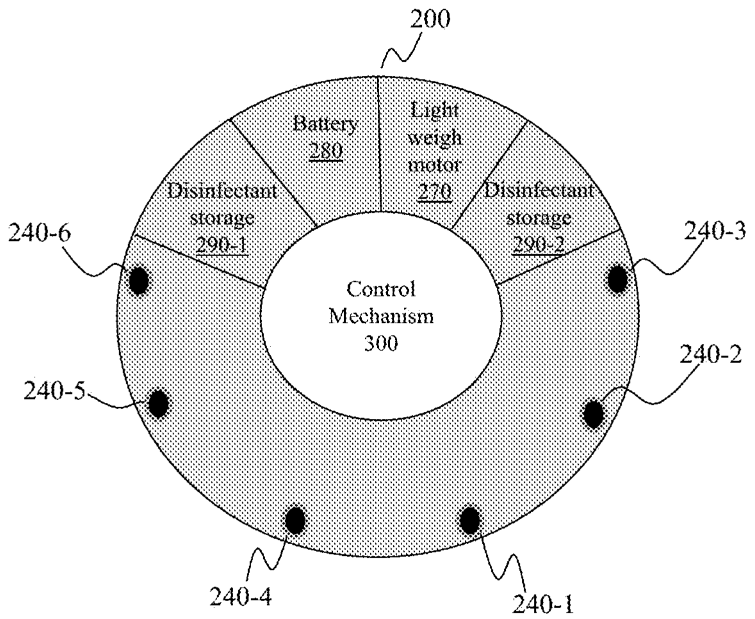
FIGS. 3G-3H depict exemplary layouts of different compartments in the back of a smart multi-function protector, in accordance with an embodiment of the present teaching.
Figure 3H:
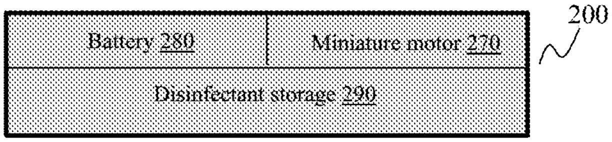

To enable different operations of the smart multi-function protector, a motor is needed to, e.g., drive the protection sheet to roll up and down. In addition, to enable sanitization, disinfectant may be stored in the smart multi-function protector 230. FIGS. 3G-3H depict exemplary layouts of different compartments in the smart multi-function protector 230, in accordance with an embodiment of the present teaching. FIG. 3G shows a top view of an exemplary layout of different compartments in the smart multi-function protector 230 arranged, e.g., in the back side of the smart multi-function protector 230. In this exemplary layout, there is a compartment 270 for storing a miniature or light weight motor for, e.g., driving the rolling of the protection sheets, another compartment 280 for storing battery that supplies power to the motor, and two more compartments 290-1 and 290-2 for storing the disinfectant. In this embodiment, these compartments are arranged along the perimeter of the head band 200 in the back. FIG. 3H provides an alternative layout in a side view of the back side of the head band 200, in accordance with another embodiment of the present teaching. In this alternative embodiment, the back of the head band 200 may be constructed with different levels, each of which may have some compartments for different components of the protector 230. In this exemplary embodiment, the storage 290 at the lower level is provided for disinfectant storage and the upper level is for storages 280 and 290 for the miniature motor and the battery.

Figure 3I:
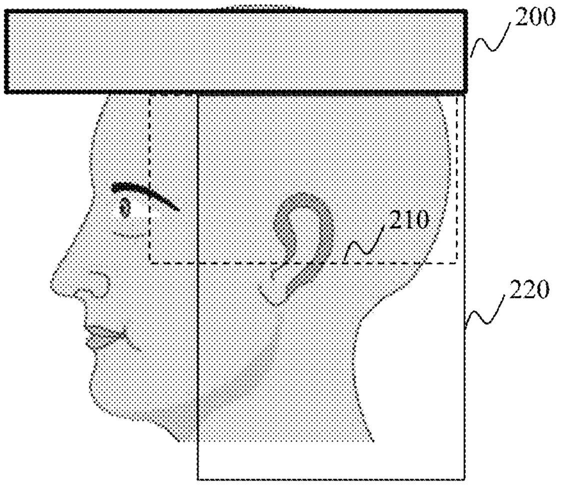
FIG. 3I illustrates an option of providing back side protection to a person wearing a smart multi-function protector, in accordance with an embodiment of the present teaching.
Figure 3J:
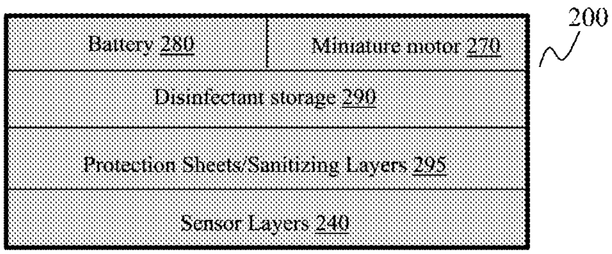
FIG. 3J presents an alternative construct of a head band 200, in accordance with an embodiment of the present teaching.

In some embodiments, the protection may be deployed all the way around the person's head. Such protection may be applied 360 degrees around or piece-wise deployed depending on the need. For example, if another person is approaching from the front, the protection may be deployed in the front as shown in FIGS. 2C-2E. In some situations, if another is approaching from the back, protection may also be needed such as what is shown in FIG. 3I. To achieve automated deployment of protection for the back side of a person, the smart multi-function protector 230 may need to acquire surround information in the back field of view 270, as shown in FIG. 3A. Sensors, protection sheet storage, and sanitizing mechanism may also be embedded in the back of the head band 200. FIG. 3J illustrates an exemplary layout of different components in the back side of the head band 200, in accordance with an embodiment of the present teaching. In this embodiment, there is a sensor layer 240 with sensors embedded to capture the surrounding information in the back field of view 270, protection sheet/sanitizing layers 295 for storing the rolled-up protection sheets and sanitizing thereof as described herein. The protection sheets in the back of the head band 200 may be stored separately from that in the front so that the deployment of the protection sheets in the back may be controlled based on different criteria, e.g., only when the need for protection is observed with respect to the back of the person. Similarly, the back sanitizing mechanism may also be controlled separately from the ones in the front and in accordance with the deployment and storage status of the protection sheets for the back side.

Although exemplary layouts of the head band 200 are provided as illustrations, other layouts are also possible and within the scope of the present teaching. For example, the entire head band 200 may have multiple levels as shown in FIG. 3J, with lowest level being the sensors, the level above sensors is for protection sheet storage and sanitizing mechanism, the level above the sanitizing mechanism may be for disinfectant storage, and other components may be provided on top of the disinfectant storage. The control criteria of the smart multi-function protector 230 for dynamically deploying protection may be similarly enforced, either with respect to the piece-wise control of protection sheets or for the overall protection sheets. Although the disclosure below regarding decision making of the smart multi-function protector 230 may be based on a specific layout or implementation, variations due to different layouts or specific implementation are all within the scope of the present teaching.

As discussed herein, the operation of the smart multi-function protector 230 is automatically controlled based on information sensed from the surrounding of a person. For instance, the sensors capture the visual information around a person and such sensor data are analyzed to, e.g., detect people moving around the person and detect the distance to each. When anyone comes within a safety distance, the protection is activated to roll down the protection sheet(s). To implement such control, the smart multi-function protector 230 may be equipped with a control mechanism 300, provided to perform functionalities for controlling the operation of the protector 230. Such functionalities may include analyzing the sensor data, determining whether there is any person in the vicinity of the protection zone of the protector, releasing the protection sheets, activating the disinfectant application, etc. The monitoring of the nearby people is continuous whenever the smart multi-function protector is worn by a person so that when there is no danger, the protection sheets are rolled back and the protection wearing the protector can have free flowing air with adequate amount of oxygen. In some embodiments, the danger may also be assessed based on whether the person is in motion or in a stable position. When the person is in a stable position, when the protection sheets are rolled up, the disinfectant is applied around the person's front, the area is kept sanitized so that even though the protection sheets are stored, the person remains safe. In some embodiments, when the person in on the move, even though there are no one in the defined safety zone, the protection sheets may still remain to be deployed because, e.g., the area the person is passing through may not be sanitized.

The control of the operation of the protector 230 is achieved by a control mechanism 300, which may or may not be physically deployed on the protector 230. In some embodiments, the control mechanism 300 may be a stand-alone programmed microprocessor capable of carrying of all necessary computations therein to control the protector. In this configuration, the control mechanism 300 is deployed on the smart multi-function protector 230 as shown in FIG. 3G, e.g., in a cap on top of the head band 200. Although illustrated on the top of the protector 230, the control mechanism 300 can reside anywhere in the protector 230, even when there is no cap over the head band. In some embodiments, the control of the protector 230 may be implemented in a client-server architecture, in which the control mechanism 300 may serve as a server guided controller that gathers data needed for the server to make a control decision, transmits the data to the server residing elsewhere, receives commands from the server, and carries out the control instructions issued by the server. In this implementation, the server may be used to control multiple smart protectors 230 and may reside in a server room in, e.g., the same building where multiple smart multi-function protectors 230 are deployed. This client-server configuration may be appropriate for a facility where multiple people need protection, such as in a medical facility such as a hospital or a doctor's office, a hotel, a conference center where employees of the facility need to provide services to other people coming to the facility.

Figure 4A:
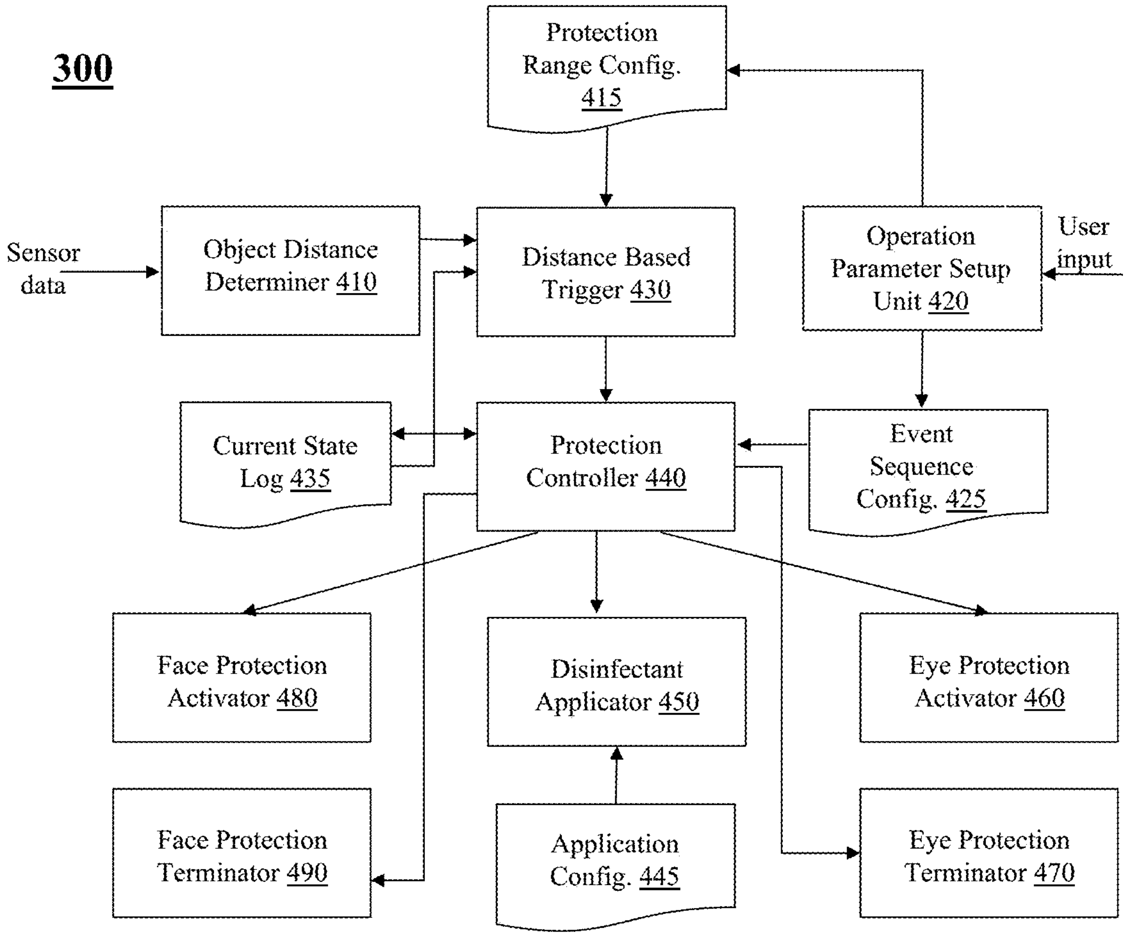
FIG. 4A depicts an exemplary high-level system diagram of a control mechanism in a smart multi-function protector, in accordance with an embodiment of the present teaching.
Figure 4B:
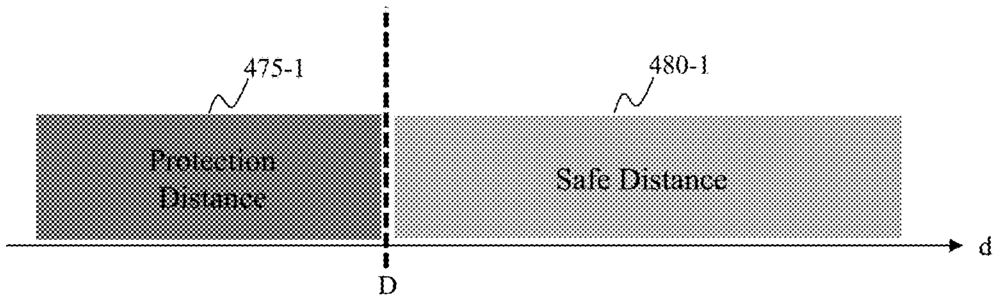
FIGS. 4B-4C illustrate different configurations of protection ranges in terms of safety distances, in accordance with an embodiment of the present teaching.
Figure 4C:
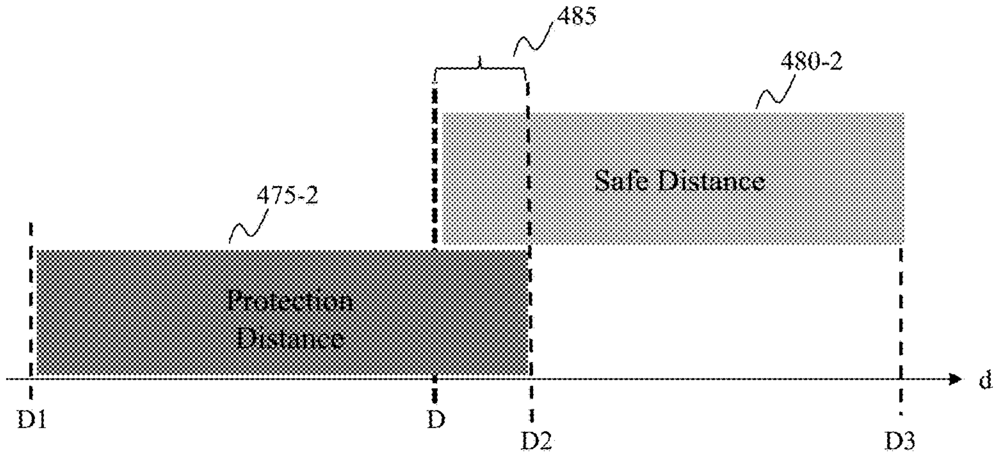

FIG. 4A depicts an exemplary high-level system diagram of a stand-alone control mechanism 300 in the smart multi-function protector 230, in accordance with an embodiment of the present teaching. In a client-server configured control scenario, some of the functionalities that can be achieved in this stand-alone system may be moved to a server. In this exemplary embodiment, the control mechanism 300 comprises an operation parameter setup unit 420, an object distance determiner 410, a distance based trigger 430, a protection controller 440, a disinfectant applicator 450, an eye protection activator 460, a face protection activator 480, an eye protection terminator 470, and a face protection determinator 490. The safety distance setup unit 420 is provided to configure the protection range. FIGS. 4B-4C illustrate different configurations of protection ranges defined based on a safety distance, in accordance with an embodiment of the present teaching. As illustrated in FIG. 4B, the protection range may be set up using multiple zones. As shown, along an axis of distance d, the protection distance 475-1 and a safe distance 480-1 may be specified and each is defined to be the distance measure from the protector 230. For example, if any person is detected within distance D from the protector 230, protection is deployed. Beyond the protection distance, the safe distance 480-1 may be defined as a range in which anyone appearing in the safe distance is to be monitored but no protection is deployed yet.

FIG. 4C shows a different configuration of protection range, in which the protection distance 475-2 is defined to extend to D2 (beyond D) and the safe distance is still starting at distance D to D3. That is, there is an overlap 485 between the protection distance and the safe distance 480-2. The protection distance may be extended to D2 when the protection is to be terminated so that it is safer. Such protection range configurations may be set up by the operation parameter setup unit 420 based on, e.g., user input. That is, the protection enforced by the smart multi-function protector 230 may be personalized. In some embodiments, there may be certain limitations built in the protector. For instance, depending on the environment or the bacteria/viruses to be prevented, the smart multi-function protector 230 may be configured with some system configurations that cannot be overridden. For instance, in a hospital, the protectors worn by medical personnel may be required to have some minimum protection distance. That is, personnel can elect to extend it to a bigger protection distance but not smaller.

Figure 5A:
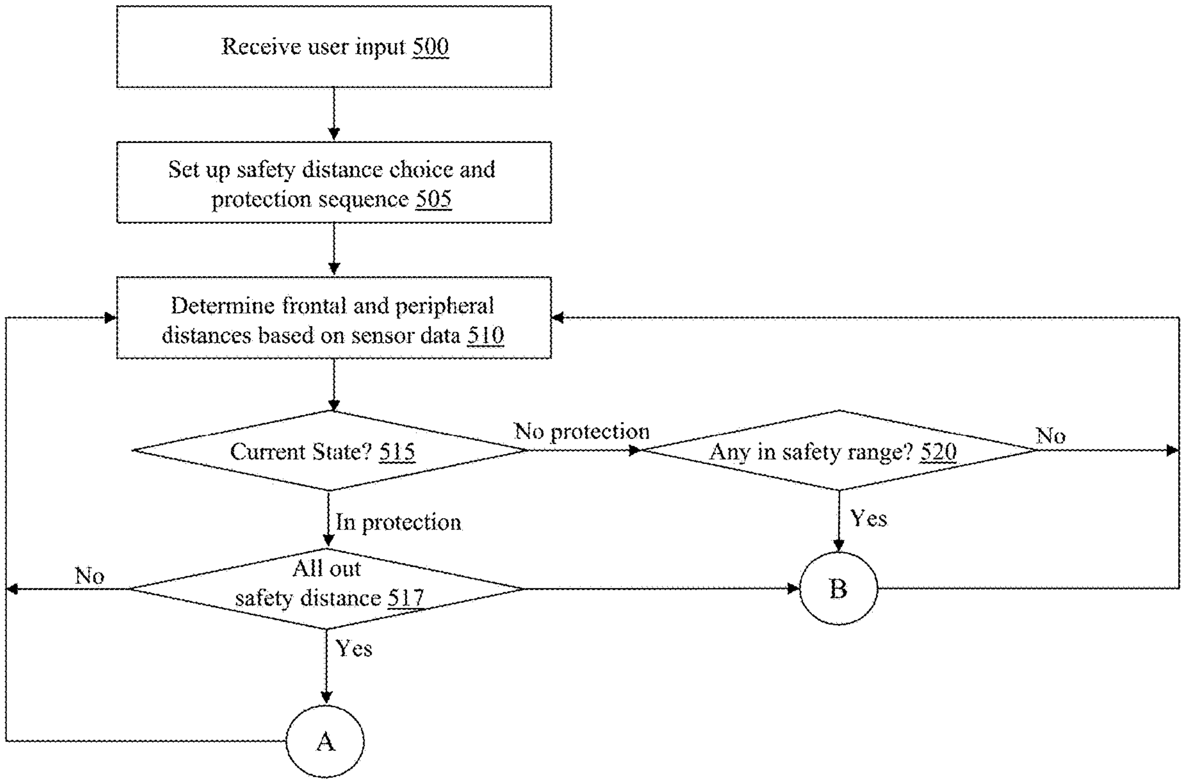
FIGS. 5A-5C show a flowchart of an exemplary process of a control mechanism in a smart multi-function protector, in accordance with an embodiment of the present teaching.
Figure 5B:
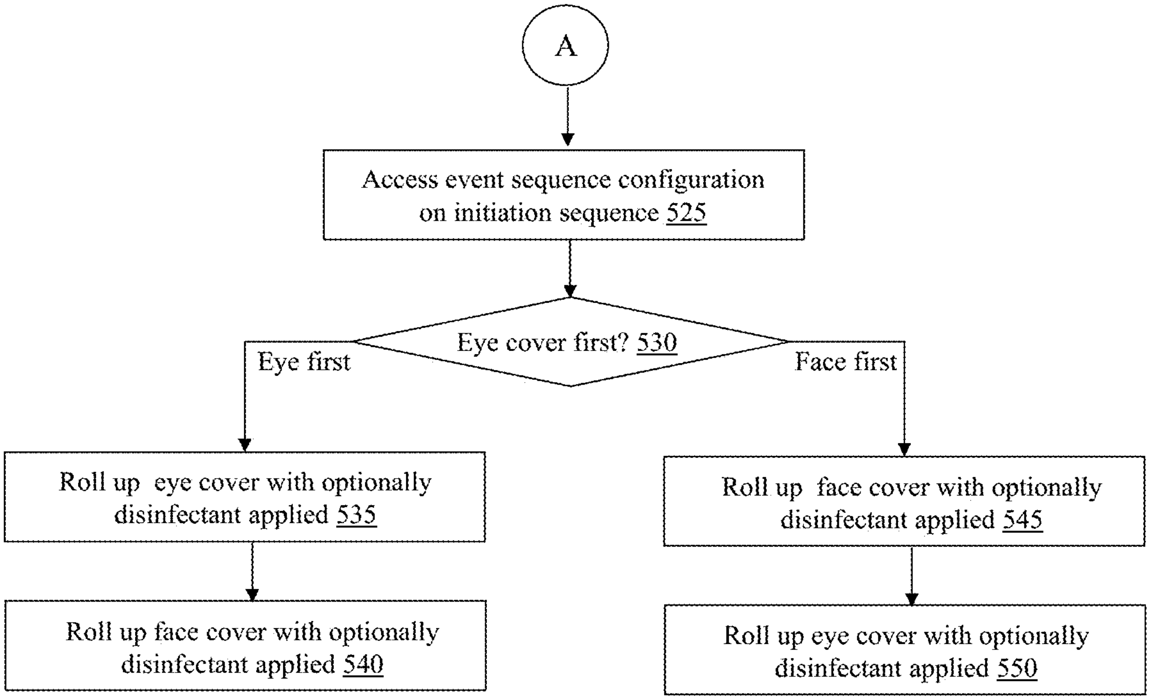
Figure 5C:
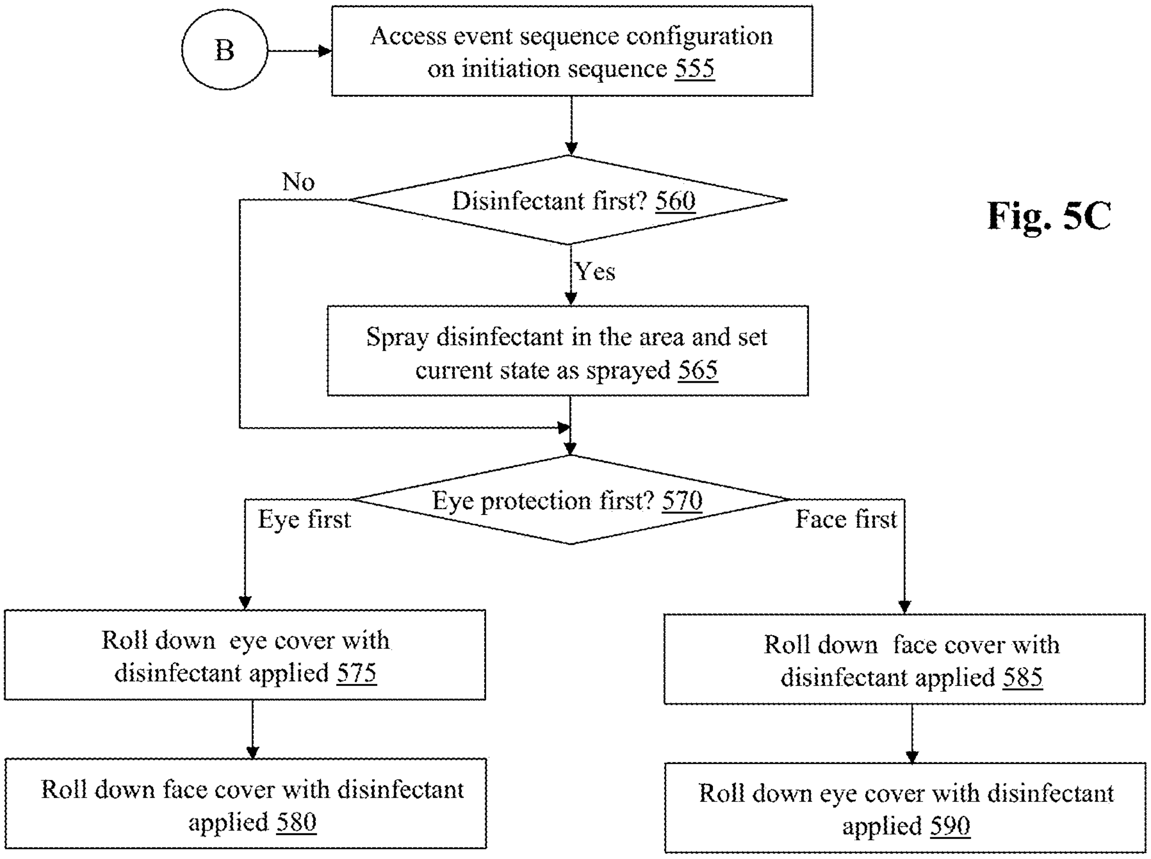

FIGS. 5A-5C show a flowchart of an exemplary process of the stand-alone control mechanism 300 deployed in a smart multi-function protector 230, in accordance with an embodiment of the present teaching. At 500, the safety distance setup unit 420 receives a user input that specifies various operational parameters, including the choices of safety protection ranges and other operation related parameters. For example, the deployment or termination of the protection may be implemented as a sequence of events and specified, e.g., in deployment or in termination, which protection sheet is release first and how long to apply disinfectant, etc. With the user input, the operation parameter setup unit 420 sets up, at 505, the safety ranges in protection range configuration 415 as well as the desired sequence of events, in an event sequence configuration 425, associated with release and termination of protection.

Once activated, various components of the control mechanism 300 in the smart multi-function protector 230 start to operate. This includes the sensors embedded around the head band 200, that acquire data capturing the surrounding of the protector 230. Based on such sensor data, the object distance determiner 410 determines, at 510, objects in front and sides nearby the protector within certain specified distance and computes the distances of such objects. Such determined distances are sent to the distance based trigger 430, which determines whether to deploy protection. To do so, the current state of the protector is checked first at 515 to see whether the protector 230 is currently in a protection mode. If so, it is further checked, at 517, whether all the objects detected are now out of the safety range. If there is still some object(s) still within the safety range, as the protector 230 is already in a protection mode, there is no need to activate protection. In this case, the processing proceeds to step 510 to continue monitoring the surroundings and detecting the distances of different objects detected therein. If all the detected objects in the surrounding are now out of the safety range, determined at 517, the distance based trigger 430 activates the protection controller 440 with an instruction to terminate the currently deployed protection. In FIG. 5A, the processing proceeds to A to terminate the current protections. Once the protection is terminated, the current state is set as without protection and the protector 230 continues to step 510 to monitor the surrounding objects.

If the current state of the protector 230 is that there is currently no protection applied, the distance based trigger 430 determines, at 520, whether any of the detected objects is now within the safety range. If none of the detected objects is in the safety range, it means that no protection is needed. In this case, the protector 230 continues to monitor the surrounding at step 510. Otherwise, protection needs to be deployed. In this case, the distance based trigger 430 activates the protection controller 440 with an instruction to deploy protection and the processing proceeds to B. After steps in B are completed, the processing returns to step 510 to continue to monitor the surrounding.

FIG. 5B is a sequence of steps to terminate protection, in accordance with an embodiment of the present teaching. As discussed herein, a smart multi-function protector 230 may be configured to terminate the protection previously deployed based on a sequence of events defined in the event sequence configuration 425. Once triggered, the protection controller 440 accesses, at 525, the even sequence configuration on how to terminate the protection. Based on the retrieved termination configuration, it is determined at 530, whether the protection needs to be terminated by terminating the eye protection first. If the configuration indicates to terminate eye protection first, the protection controller 440 invokes the eye protection terminator 470 first to terminate the protection by rolling up, at 535, the 1$^{st}$ protection sheet 210. In some circumstances, disinfectant may also be applied while rolling up the protection sheet to sanitize the 1$^{st}$ protection sheet and the nearby area. After that, the protection controller 440 invokes the face protection terminator 490 to roll up, at 540, the 2$^{nd}$ protection sheet 220. Similarly, disinfectant may be applied to sanitize the 2$^{nd}$ protection sheet and the nearby area when it is rolled up.

If it is configured to terminate the face protection first, determined at 530, the protection controller 440 activates the face protection terminator 490 to roll up, at 545, the 2$^{nd}$ protection sheet 220. In some circumstances, disinfectant may also be applied to sanitize the 2$^{nd}$ protection sheet while it is rolled up and the nearby area. After that, the protection controller 440 invokes the eye protection terminator 470 to roll up, at 550, the 1$^{st}$ protection sheet 210. Similarly, disinfectant may be applied to sanitize the 1$^{st}$ protection sheet 210 and the nearby area.

FIG. 5C depicts the flowchart of the process to deploy the protection, in accordance with an embodiment of the present teaching. The process B of FIG. 5C is initiated when there is a need to deploy protection (e.g., when there is some object(s) within the safety range) when the protection is not put in place, as shown in FIG. 5A. To deploy protection, the protection controller 440 is invoked with an instruction to apply protection. The protection controller 440 accesses, at 555, the configuration of sequence of events to initiate the protection. Based on the configured sequence of events, it is determined, at 560, whether disinfectant is to be applied first before or while the protection sheets are to be rolled out from storages. If it is configured to sanitize the protection sheets, the protection controller 440 controls to have, e.g., spray holes to spray, at 565, the disinfectant onto or around the protection sheets to be deployed. If the configuration specifies that no disinfectant is needed (e.g., the protection sheets have been sanitized before storage), then no application of sanitization.

The deployment of the protection sheets may also be controlled based on the sequence or order of events specified in the configuration. If the configuration indicates to deploy eye protection first, determined at 570, the protection controller 440 invokes the eye protection activator 460 to rolling down, at 575, the 1$^{st}$ protection sheet 210. The disinfectant is then applied while rolling down the protection sheet to sanitize the 1$^{st}$ protection sheet and the nearby area. After that, the protection controller 440 invokes the face protection activator 480 to roll down, at 580, the 2$^{nd}$ protection sheet 220. Similarly, disinfectant may be applied to sanitize the 2$^{nd}$ protection sheet and the nearby area when it is rolled down. If it is configured to terminate the face protection first, determined at 570, the protection controller 440 activates the face protection activator 480 to roll down, at 585, the 2$^{nd}$ protection sheet 220. Disinfectant may also be applied to sanitize the 2$^{nd}$ protection sheet while it is rolled down and the nearby area. After that, the protection controller 440 invokes the eye protection activator 460 to roll down, at 590, the 1$^{st}$ protection sheet 210. Similarly, disinfectant may be applied to sanitize the 1$^{st}$ protection sheet 210 and the nearby area.

Figure 6A:
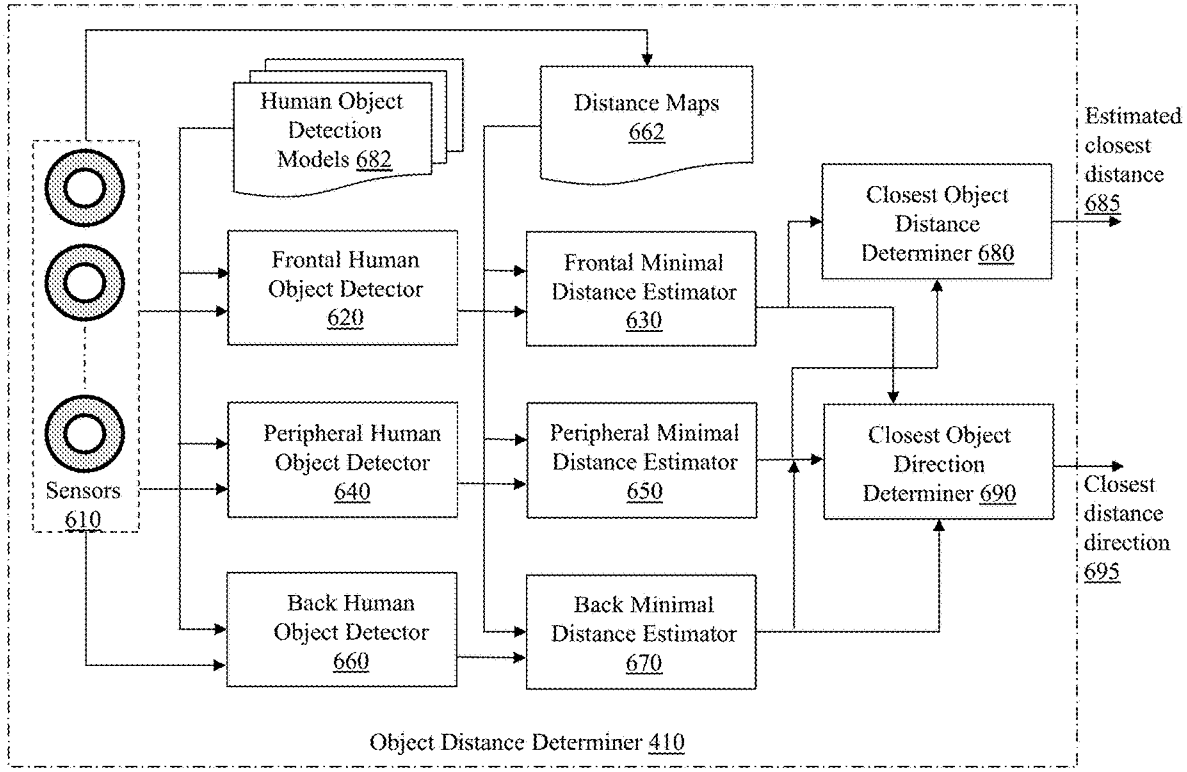
FIG. 6A depicts an exemplary high-level system diagram of an object distance determiner, in accordance with an embodiment of the present teaching.

As discussed herein, to overcome the issues encountered using prior art solutions for protection, the present teaching aims to achieve dynamically deploying protection only when there is a detected need, e.g., when other(s) is nearby. This is by monitoring the surrounding, detecting any situation where a dynamic need arises, creating a safe micro-environment for a user, and deploying/storing the protection sheets on a need basis. Due to the nature of the problem, the dynamic decisions rely on the determination of whether there is any other person within a specified distance from the person wearing the protector 230 and if so, in which direction. FIG. 6A depicts an exemplary high-level system diagram of the object distance determiner 410, in accordance with an embodiment of the present teaching. As shown in FIG. 4, the object distance determiner 410 takes sensor data as input and generates an output relating to another person detected as closest to the protector 230 in the specified safety range. In some embodiments, the output may include, e.g., a distance and a direction of the other person, e.g., front, left, right, or back. These parameters are used by the distance based trigger 430 to decide whether protection is needed and if so, which side of the protector to deploy the protection.

In the illustrated embodiment in FIG. 6A, the object distance detector 410 comprises a frontal human object detector 620, a frontal minimum distance estimator 630, a peripheral human object detector 640, a peripheral minimal distance estimator 650, a back human object detector 660, a back minimal distance estimator 670, a closest object distance determiner 680, and a closest object direction determiner 690. The frontal human object detector 620, the peripheral human object detector 640, and the back human object detector 660 are provided to detect whether there are any humans in their respective fields of view (front, left, right, and back) based on data from sensors designated to capture the surrounding information in such fields of view. The detection of nearby humans may use human object detection models 682, which may be trained via machine learning based on training data. In some embodiments, the detection of presence of nearby humans may be executed based on, e.g., visual data from camera sensors. For instance, presence of humans may be detected based on human skin tones, modeled by skin detection models in 682. Using this approach, regions of interest in visual data may be identified as representation of human faces and can direct subsequent processing quickly to focused areas to improve processing efficiency. Such detected nearby humans may be in different directions, including in the front, on the left or right, or in the back.

The purpose for detecting nearby humans is for determining whether any of such nearby humans are within the specified safety ranges. In some embodiments, the safety range in different directions may be defined to be the same. In some embodiments, the safety range for some direction may be different from that of others. For instance, the safety distance for the front may be set larger so that the protection decision is more conservative because, e.g., most of the open organs of a person are in the front of a person's face. The safety range for the back may be set smaller, i.e., the protection may be deployed when another person is closer in the back. To see whether any of the detected nearby humans is within a relevant specified safety range, a minimal distance to a detected nearby human in each direction may be determined. This is performed by the frontal minimal distance estimator 630, the peripheral minimal distance estimator 650, and the back minimal distance estimator 670, respectively. In some embodiments, a distance to each of the nearby humans detected in a direction (e.g., front) may be estimated first and the smallest distance to one such detected person is selected as the minimal distance in that direction. In some embodiments, the distance to each detected nearby human may be estimated based on, e.g., stereo or from a distance map of the region in that director generated by a depth sensor. For instance, a depth sensor may be designated to capture a depth map in each of the 4 directions. Such a depth sensor may be calibrated with a visual sensor for the same direction.

In some embodiments, the distance to each of the detected nearby human may be estimated by using sensor data in multiple modalities. For example, each of the human faces detected in a visual image in a specific field of view (e.g., front), pixels in a depth map acquired in the same direction corresponding to the human face region in a visual image may be identified and values in such corresponding pixels represent distances from the human face to the smart multi-function protector 230. In some embodiments, a smallest distance value from all depth map pixels corresponding to a human face may be used to represent the distance between the detected human and the protector 230. In some embodiments, an average distance may be computed based on distance values from all depth map pixels corresponding to a human face may be used to represent the distance between the detected human and the protector 230. In this manner, the frontal minimal distance estimator 630 estimates the minimal distance of a human detected in the front as the closest human to the protector 230. The peripheral minimal distance estimator 650 estimates the minimal distance of a human detected in a peripheral direction (left or right) as the closest human to the protector 230. The back minimal distance estimator 670 estimates the minimal distance of a human detected in the back direction as the closest human to the protector 230.

With the minimal distances in different directions estimated, the closest object distance determiner 680 may then compare the minimal distances from different directions and select one that is the smallest among all directions and this smallest distance is to be used to determine whether it is within the specified safety distance in a relevant direction. To make that determination, the direction in which the nearby human closest to the protector is also determined by the closest object direction determiner 690. The smallest distance output by the closest object distance determiner 680 and the direction of the closest nearby human output by the closest object direction determiner 690 are then sent to the distance based trigger 430 to determine whether the protection is to be deployed.

Figure 6B:
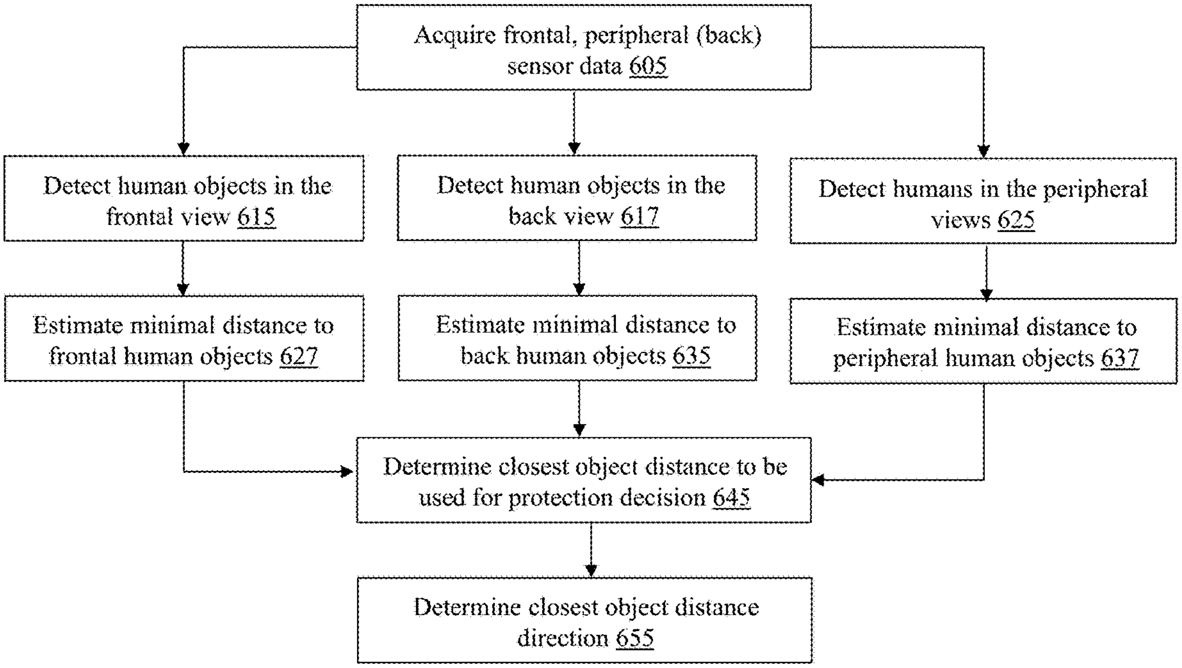
FIG. 6B is a flowchart of an exemplary process of an object distance determiner, in accordance with an embodiment of the present teaching.

FIG. 6B is a flowchart of an exemplary process of the object distance determiner 410, in accordance with an embodiment of the present teaching. At 605, via sensors embedded in the head band 200, frontal, back, and peripheral sensor data are acquired to capture the surrounding information nearby the smart multi-function protector 230. Such acquired data are used by different processing components to detect nearby humans in each direction and estimate the distances of such nearby humans. Specifically, the frontal human object detector 620 detects, at 615, nearby humans appearing in the front field of view. The frontal minimal distance estimator 630 then estimates, at 627, the minimal distance of a nearby human detected in the front. The peripheral human object detector 640 detects, at 625, nearby humans appearing in the peripheral field of view. This processing includes both processing sensor data from both left and right fields of view. Then the peripheral minimal distance estimator 650 estimates, at 637, the minimal distance of a nearby human detected in the left and right sides of the protector 230. Optionally, if the back of the protector 230 is also configured with sensors and protection sheets, the back human object detector 660 detects, at 617, nearby humans appearing in the back field of view. Then the back minimal distance estimator 660 estimates, at 635, the minimal distance of a nearby human detected in the back area of the protector 230. Based on the closest distances estimated in different directions, the closest object distance determiner 680 and the closest object direction determiner 690 select, respectively, the closest nearby human detected around the protector 230 and its corresponding direction so that a decision as to whether to deploy the protection is made based on such estimates in accordance with the disclosure presented herein.

Figure 7:
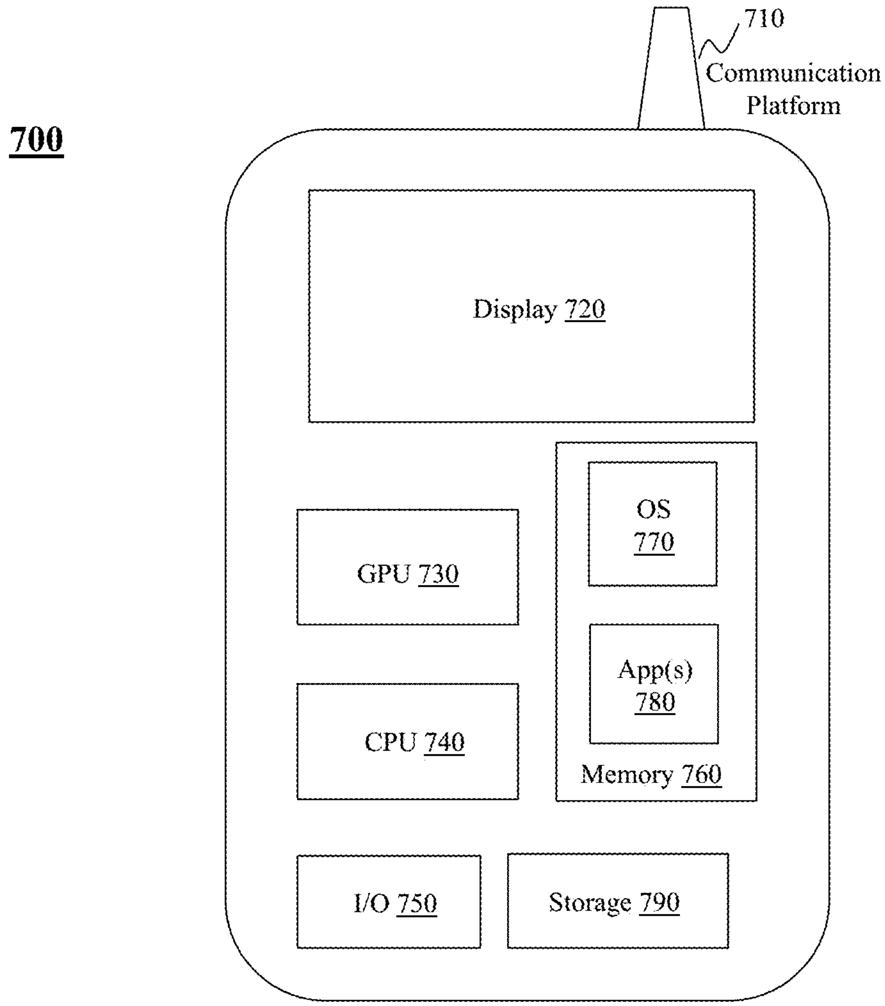
FIG. 7 is an illustrative diagram of an exemplary mobile device architecture that may be used to realize a specialized system implementing the present teaching in accordance with various embodiments.

FIG. 7 is an illustrative diagram of an exemplary mobile device architecture that may be used to realize a specialized system implementing the present teaching in accordance with various embodiments. In this example, the user device on which the present teaching may be implemented corresponds to a mobile device 700, including, but not limited to, a smart phone, a tablet, a music player, a handled gaming console, a global positioning system (GPS) receiver, and a wearable computing device, or in any other form factor. Mobile device 700 may include one or more central processing units ("CPUs") 740, one or more graphic processing units ("GPUs") 730, a display 720, a memory 760, a communication platform 710, such as a wireless communication module, storage 790, and one or more input/output (I/O) devices 750. Any other suitable component, including but not limited to a system bus or a controller (not shown), may also be included in the mobile device 700. As shown in FIG. 7, a mobile operating system 770 (e.g., iOS, Android, Windows Phone, etc.), and one or more applications 780 may be loaded into memory 760 from storage 790 in order to be executed by the CPU 740. The applications 780 may include a user interface or any other suitable mobile apps for information analytics and management according to the present teaching on, at least partially, the mobile device 700. User interactions, if any, may be achieved via the I/O devices 750 and provided to the various components connected via network(s).

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to appropriate settings as described herein. A computer with user interface elements may be used to implement a personal computer (PC) or other type of workstation or terminal device, although a computer may also act as a server if appropriately programmed. It is believed that those skilled in the art are familiar with the structure, programming, and general operation of such computer equipment and as a result the drawings should be self-explanatory.

Figure 8:
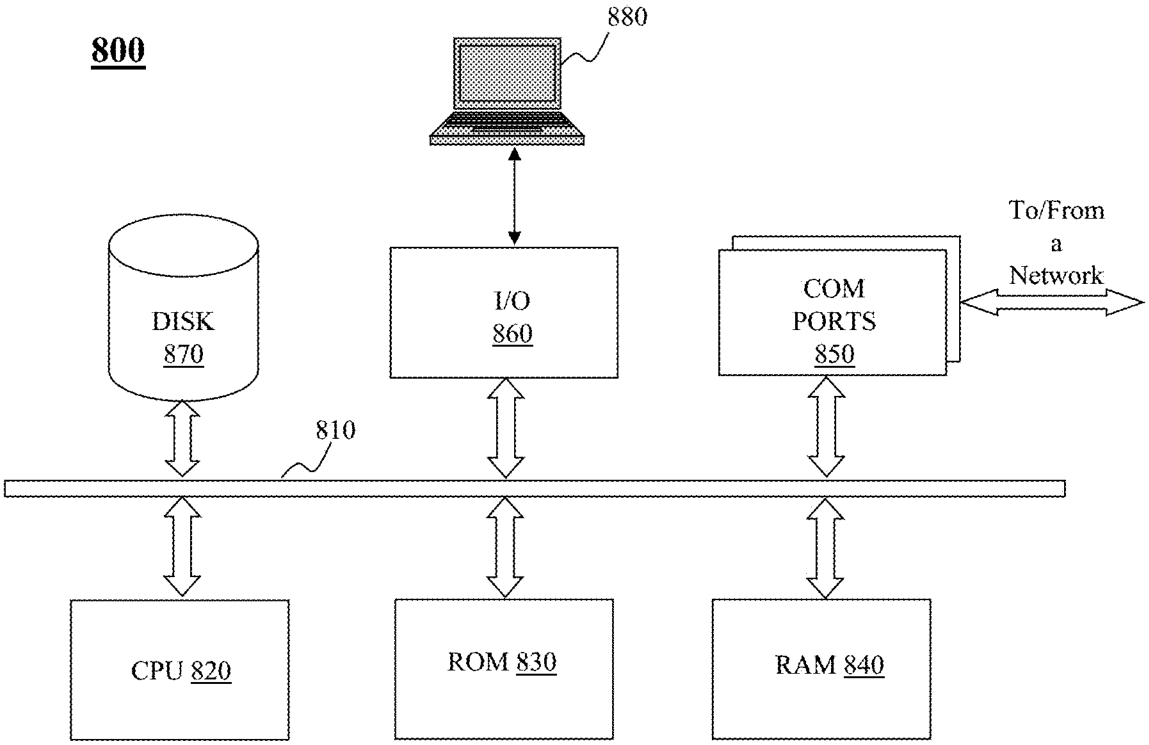
FIG. 8 is an illustrative diagram of an exemplary computing device architecture that may be used to realize a specialized system implementing the present teaching in accordance with various embodiments.

FIG. 8 is an illustrative diagram of an exemplary computing device architecture that may be used to realize a specialized system implementing the present teaching in accordance with various embodiments. Such a specialized system incorporating the present teaching has a functional block diagram illustration of a hardware platform, which includes user interface elements. The computer may be a general-purpose computer or a special purpose computer. Both can be used to implement a specialized system for the present teaching. This computer 800 may be used to implement any component or aspect of the framework as disclosed herein. For example, the information analytical and management method and system as disclosed herein may be implemented on a computer such as computer 800, via its hardware, software program, firmware, or a combination thereof. Although only one such computer is shown, for convenience, the computer functions relating to the present teaching as described herein may be implemented in a distributed fashion on a number of similar platforms, to distribute the processing load.

Computer 800, for example, includes COM ports 850 connected to and from a network connected thereto to facilitate data communications. Computer 800 also includes a central processing unit (CPU) 820, in the form of one or more processors, for executing program instructions. The exemplary computer platform includes an internal communication bus 810, program storage and data storage of different forms (e.g., disk 870, read only memory (ROM) 830, or random-access memory (RAM) 840), for various data files to be processed and/or communicated by computer 800, as well as possibly program instructions to be executed by CPU 820. Computer 800 also includes an I/O component 860, supporting input/output flows between the computer and other components therein such as user interface elements 880. Computer 800 may also receive programming and data via network communications.

Hence, aspects of the methods of dialogue management and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, in connection with information analytics and management. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the techniques as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

I claim:

1. A method implemented on at least one processor, a memory, and a communication platform for dynamically deploying protection to a user, comprising:

receiving data from a plurality of sensors embedded in a protector, worn by a user on head and configured for providing protection to the user based on need, wherein the data capture information surrounding the user;

detecting, based on the data, one or more people appearing nearby the user;

estimating, dynamically, a distance between the user and each of the one or more people;

if a current state of the protector is a protection state, monitoring the dynamically changing distances between the user and the one or more people, retracting the protection when the distances satisfy a first condition, and setting the current state to a no-protection state; and if the current state is a no-protection state, estimating, based on the distances between the user and the one or more people, a closest distance between the user and any of the one or more people, applying, if the closest distance satisfies a second condition, the protection to the user by releasing at least one protection shield stored in the protector to create a barrier between the user and the one or more people, and setting the current state to a protection state.

2. The method of claim 1, wherein the plurality of sensors includes at least one of:

one or more visual sensors; and one or more depth sensors, wherein the plurality of sensors are arranged along the perimeter of a head band of the protector to provide means to monitor the surrounding information around the protector in different fields of view along different directions.

3. The method of claim 2, wherein the different fields of view in different directions include:

a front field of view in a direction extending forward from the face of the user;

a left peripheral field of view in a direction extending to the left from the left ear of the user;

a right peripheral field of view in a direction extending to the right from the right ear of the user; and a back field of view in a direction extending to the back of the user.

4. The method of claim 1, wherein the at least one protection shield includes at least one of:

a first protection shield provided for protecting a first portion of the user, which can be retracted into the head band of the protector or released therefrom to create a first barrier between the first portion of the user and surrounding of the user;

a second protection shield provided for protecting a second portion of the user, which can be retracted into the head band of the protector or released therefrom to create a second barrier between the second portion of the user and surrounding of the user, wherein the first and second protection shields are separately retracted, stored, and released.

5. The method of claim 1, wherein the protector includes a first storage for storing the at least one protection shield when retracted, a second storage for storing disinfectant used to sanitize the at least one protection shield, and one or more spray heads for applying the disinfectant to the at least one protection shields when activated.

6. The method of claim 5, wherein the one or more spray heads applies the disinfectant to at least one of:

the at least one protection shield when the at least one protection shield is in a process of being retracted to ensure that the at least one protection shield is sanitized before being stored in the first storage, and the at least one protection shield is being released to create corresponding barrier to ensure that the barrier is sanitized; and a space between the user's face and the at least one protection shield when the at least one protection shield is released from the first storage of the protector.

7. The method of claim 1, wherein the first condition specifies that none of the monitored distances is within a safety range; and the second condition specifies that the closest distance comes within a protection range, wherein the safety range and the protection range are disjoint or overlap.

8. The method of claim 1, wherein the step of retracting the protection comprises:

accessing a first event sequence specifying a first order to retracting the at least one protection shield;

sanitizing each of the at least one protection shield currently deployed for protection in the first order; and rolling back each of the disinfected at least one protection shield in the first order.

9. The method of claim 1, wherein the step of applying the protection comprises:

accessing a second event sequence specifying a second order to release the at least one protection shield;

sanitizing each of the at least one protection shield to be released from the protector in the second order; and releasing each of the disinfected protection shield in the second order.

10. A machine readable and non-transitory medium having information recorded thereon, wherein the information, when read by the machine, causes the machine to perform the following steps:

receiving data from a plurality of sensors embedded in a protector, worn by a user on head and configured for providing protection to the user based on need, wherein the data capture information surrounding the user;

detecting, based on the data, one or more people appearing nearby the user;
estimating, dynamically, a distance between the user and each of the one or more people;
if a current state of the protector is a protection state,
monitoring the dynamically changing distances between the user and the one or more people,
retracting the protection when the distances satisfy a first condition, and
setting the current state to a no-protection state; and
if the current state is a no-protection state,
estimating, based on the distances between the user and the one or more people, a closest distance between the user and any of the one or more people,
applying, if the closest distance satisfies a second condition, the protection to the user by releasing at least one protection shield stored in the protector to create a barrier between the user and the one or more people, and
setting the current state to a protection state.

11. The medium of claim 1, wherein
the first condition specifies that none of the monitored distances is within a safety range; and
the second condition specifies that the closest distance comes within a protection range, wherein
the safety range and the protection range are disjoint or overlap.

12. The medium of claim 10, wherein the step of retracting the protection comprises:
accessing a first event sequence specifying a first order to retracting the at least one protection shield;
sanitizing each of the at least one protection shield currently deployed for protection in the first order; and
rolling back each of the disinfected at least one protection shield in the first order.

13. The medium of claim 10, wherein the step of applying the protection comprises:
accessing a second event sequence specifying a second order to release the at least one protection shield;
sanitizing each of the at least one protection shield to be released from the protector in the second order; and
releasing each of the disinfected protection shield in the second order.

14. A protector for dynamically providing protection to a user, comprising:
a head band constructed for being worn by a user around the head, including
at least one protection shield, each of which is constructed with a flex material so that it can be retracted to and released from the head band to create a barrier between the head of the user wearing the protector and surrounding environment,
a first storage for storing each of the at least one protection shield when it is retracted,
at least one second storage for storing disinfectant used to sanitize the at least one protection shield,
a plurality of sensors embedded along the perimeter of the head band and configured for monitoring surrounding of the user, and
a protection control mechanism configured for continually analyzing data from the plurality of sensors to dynamically deploy the at least one protection shield to protect the user when a need arises based on the analysis.

15. The protector of claim 14, wherein the head band further comprises:
a sanitizing mechanism configured for applying disinfectant to selected at least one protection shield and between specified space between some protection shields, wherein the sanitizing mechanism includes one or more application units for dispensing disinfectant to the at least one protection sheet and/or surrounding; and
a miniature motor configured for driving the retraction and release of each of the at least one protection shield.

16. The protector of claim 14, wherein the protection control mechanism comprises:
a distance determiner implemented by a processor and configured for
receiving data from the plurality of sensors with information capturing the surrounding the user to detect one or more people appearing nearby the user, and
tracking, based on the data, a distance between each of the one or more people and the user; and
a protection controller implemented by a processor and configured for determining, based on the tracked distances,
if a current state of the protector is a protection state,
monitoring the tracked distances between the user and the one or more people,
retracting the protection when the distances satisfy a first condition, and
setting the current state to a no-protection state; and
if the current state is a no-protection state,
estimating, based on the tracked distances, a closest distance between the user and the one or more people,
applying, if the closest distance satisfies a second condition, the protection to the user by releasing at least one protection shield stored in the protector to create a barrier between the user and the one or more people, and
setting the current state to a protection state.

* * * * *